(12) United States Patent
Probst et al.

(10) Patent No.: US 6,946,220 B2
(45) Date of Patent: Sep. 20, 2005

(54) ELECTROCHEMICAL CELL HAVING A MULTIPLATE ELECTRODE ASSEMBLY HOUSED IN AN IRREGULARLY SHAPED CASING

(75) Inventors: Joseph M. Probst, Williamsville, NY (US); Scott P. Hall, North Tonawanda, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 254 days.

(21) Appl. No.: 10/272,185

(22) Filed: Oct. 16, 2002

(65) Prior Publication Data

US 2003/0077509 A1 Apr. 24, 2003

Related U.S. Application Data

(60) Provisional application No. 60/359,317, filed on Oct. 19, 2001.

(51) Int. Cl.$^7$ .............................................. H01M 6/12
(52) U.S. Cl. ...................... 429/162; 429/151; 429/161; 429/163
(58) Field of Search ............................... 429/152, 161, 429/162, 163

(56) References Cited

U.S. PATENT DOCUMENTS

| | | |
|---|---|---|
| 473,841 A | 4/1892 | Hulin |
| 2,307,766 A | 1/1943 | Deibel |
| 2,715,652 A | 8/1955 | Chubb et al. |
| 2,870,235 A | 1/1959 | Soltis |
| 3,169,889 A | 2/1965 | Zahn |
| 3,345,211 A | 10/1967 | Lafon et al. |
| 3,740,270 A | 6/1973 | Bilhorn |
| 3,770,505 A | 11/1973 | Bergum et al. |
| 3,928,069 A | 12/1975 | Sperandio et al. |
| 4,007,472 A | 2/1977 | Land |
| 4,028,479 A | 6/1977 | Fanicullo et al. |
| 4,047,289 A | 9/1977 | Wolff |
| 5,045,415 A | 9/1991 | Witehira |
| 5,323,527 A | 6/1994 | Ribordy et al. |
| 5,401,595 A | 3/1995 | Kagawa et al. |
| 5,604,051 A | 2/1997 | Pulley et al. |
| 6,610,443 B2 * | 8/2003 | Paulot et al. ................ 429/181 |
| 6,635,381 B2 * | 10/2003 | Spillman et al. ............. 429/161 |

FOREIGN PATENT DOCUMENTS

| | | |
|---|---|---|
| EP | 0 771 037 A1 | 2/1997 |
| EP | 0 928 035 A1 | 7/1999 |
| EP | 0 901 177 A2 | 10/1999 |
| JP | 06181069 | 6/1994 |

* cited by examiner

Primary Examiner—Dah-Wei Yuan
(74) Attorney, Agent, or Firm—Michael F. Scalise

(57) ABSTRACT

An economical method for manufacturing an electrode assembly of virtually any shape to fit into a similarly shaped casing without compromising volumetric efficiency is described. This is accomplished by providing an electrode assembly of multiplate anode and cathode plates that substantially match the internal shape of the casing. That way, no matter what shape the device being powered by the cell dictates the electrode assembly assumes, as little internal volume as possible is left unoccupied by electrode active materials.

27 Claims, 8 Drawing Sheets

ELECTROCHEMICAL CELL HAVING A MULTIPLATE ELECTRODE ASSEMBLY HOUSED IN AN IRREGULARLY SHAPED CASING

CROSS REFERENCE TO RELATED APPLICATION

This application claims priority based on provisional application Ser. No. 60/359,317, filed Oct. 19, 2001.

BACKGROUND OF THE INVENTION

1. Field of the Invention

The present invention generally relates to the conversion of chemical energy to electrical energy, and more particularly, to an alkali metal electrochemical cell. The cell can be of either a primary chemistry, for example a lithium/silver vanadium oxide (Li/SVO) cell, or a secondary chemistry, for example a lithium-ion secondary cell.

Currently, lithium-based primary and secondary cells are used in a large number of medical and commercial applications including implantable medical devices, telephones, camcorders and other portable electronic equipment. They come in a variety of shapes, sizes and configurations as coin, button, and cylindrical and prismatic cells. There are several other applications, however, for which lithium-containing cells may be used but for which present day constructions are unsuitable. Such applications include the next generation of medical instruments, implantable medical devices and surgical tools. For many of these applications, the use of prior art lithium-containing cells is unacceptable because of their shape and construction. In certain types of medical applications, irregularly shaped prismatic cells that are sized for use within the human body are most preferred.

2. Prior Art

Currently, lithium-containing cells are used to power a number of implantable medical devices including ventricular assist devices, artificial hearts and implantable hearing aids, among others. The predominantly used method for manufacturing such cells is to position a single anode and a single cathode overlaying each other with an intermediate separator sandwiched between them. This electrode assembly is then wound together about a mandrel.

A representative wound cell electrode assembly 10 is shown in FIG. 1. The electrode assembly 10 comprises an anode electrode 12 and a cathode electrode 14 disposed on either side of an intermediate separator 16. This anode/separator/cathode structure is then positioned on a plate-shaped mandrel having opposed planar sides (not shown) that is rotated to provide the wound assembly shown. The resulting wound electrode assembly 10 has relatively planar opposed sides 18 and 20 extending to curved ends 22 and 24. The upper and lower edges (only upper edge 26 is shown) of the anode 12, cathode 16 and intermediate separator 14 are also relatively planar.

The electrode assembly 10 is then housed in a prismatic-shaped casing 28 (FIG. 2A) of a deep drawn type. Casing 28 is comprised of opposed major face walls 30 and 32 extending to and meeting with generally planar end walls 34 and 36 at curved corners. The face walls 30, 32 and end walls 34, 36 connect to a planar bottom wall 38. A lid 40 secured to the upper edges of face walls 30, 32 and end walls 34, 36, such as by welding, closes the casing. The lid 40 supports a terminal lead 42 insulated from the lid and casing 28 by a glass-to-metal seal 44. There is also a fill opening 46 in the lid closed by a closure means 48, as is well known by those skilled in the art. The lead 42 is connected to one of the electrodes, typically the cathode, while the casing 28 and lid 40 serve as the lead for the other electrode, typically the anode. This describes a case-negative cell design.

FIG. 2B shows a cylindrically-shaped casing 50 closed by a lid 52 supporting a glass-to-metal seal 54 insulating a terminal lead 56 from the lid. Casing 50 is similar to the casing 28 of FIG. 2A except that it is cylindrical instead of being of a prismatic shape. In this case, the mandrel used to wind the electrode assembly is of a cylindrically shaped rod.

Winding an anode/separator/cathode structure limits the geometric configuration of the resulting cell to cylindrical or generally rectangular shapes. In some applications, these shapes are inefficient because the internal casing volume is grossly under-utilized. For example, the curved ends 20, 22 of electrode assembly 10 fit well into the ends 34, 36 of the prismatic-shaped casing 10 (FIG. 2A) and the upper 26 and lower edges fairly match the shape of the lid 40 and bottom wall 38, respectively. However, if the bottom wall of casing 10 is shaped other than relatively planar, that would not be true. Depending on the shape of the bottom wall 38, there could be a large volume of unused space inside the casing. This is because it is difficult to provide wound electrode assemblies having other than planar upper and lower edges. The use of multiplate electrode assemblies according to the present invention rectifies this problem.

Accordingly, a need exists for electrochemical cells that are, among other things, of a multiplate construction and suitably configured for housing in casings of other than the traditional prismatic shape (FIG. 2A) or cylindrical shape (FIG. 2B). Such "irregularly shaped" electrode assemblies and the casings that house them are particularly well suited for powering implantable medical devices, and the like. Medical devices are being implanted in increasingly disparate parts of the body. For this reason, they must be of varied shapes and sizes, which, in turn, drives the shape of the associated power source. Thus, a process is needed for manufacturing electrochemical cells having shapes that take advantage of as much of the internal volume in a casing, even one of an irregular shape, as possible.

SUMMARY OF THE INVENTION

The present invention describes an economical method for manufacturing an electrode assembly of virtually any shape to fit into a similarly shaped casing without compromising volumetric efficiency. This is accomplished by providing an electrode assembly of a multiplate design. The anode and the cathode plates are shaped to substantially match the internal shape of the casing. That way, no matter what shape the medical device dictates the electrode assembly assume, as little internal volume as possible inside the casing is left unoccupied by electrode active materials.

These features of the present invention will become increasingly more apparent to those skilled in the art by reference to the following detailed description of the preferred embodiments and the appended drawings.

DETAILED DESCRIPTION OF THE PREFERRED EMBODIMENT

The benefits of the present invention are best understood by first illustrating an irregularly shaped casing housing an electrochemical cell. Irregularly shaped casings are becoming increasingly more common, especially in implantable medical devices. These include cardiac defibrillators, cardiac pacemakers, neuro-stimulators, drug pumps, and the like. Such medical devices are designed to reside inside the body so that their shape is as unobtrusive as possible. This, in turn, dictates the shape of the associated power source.

Figure 3:
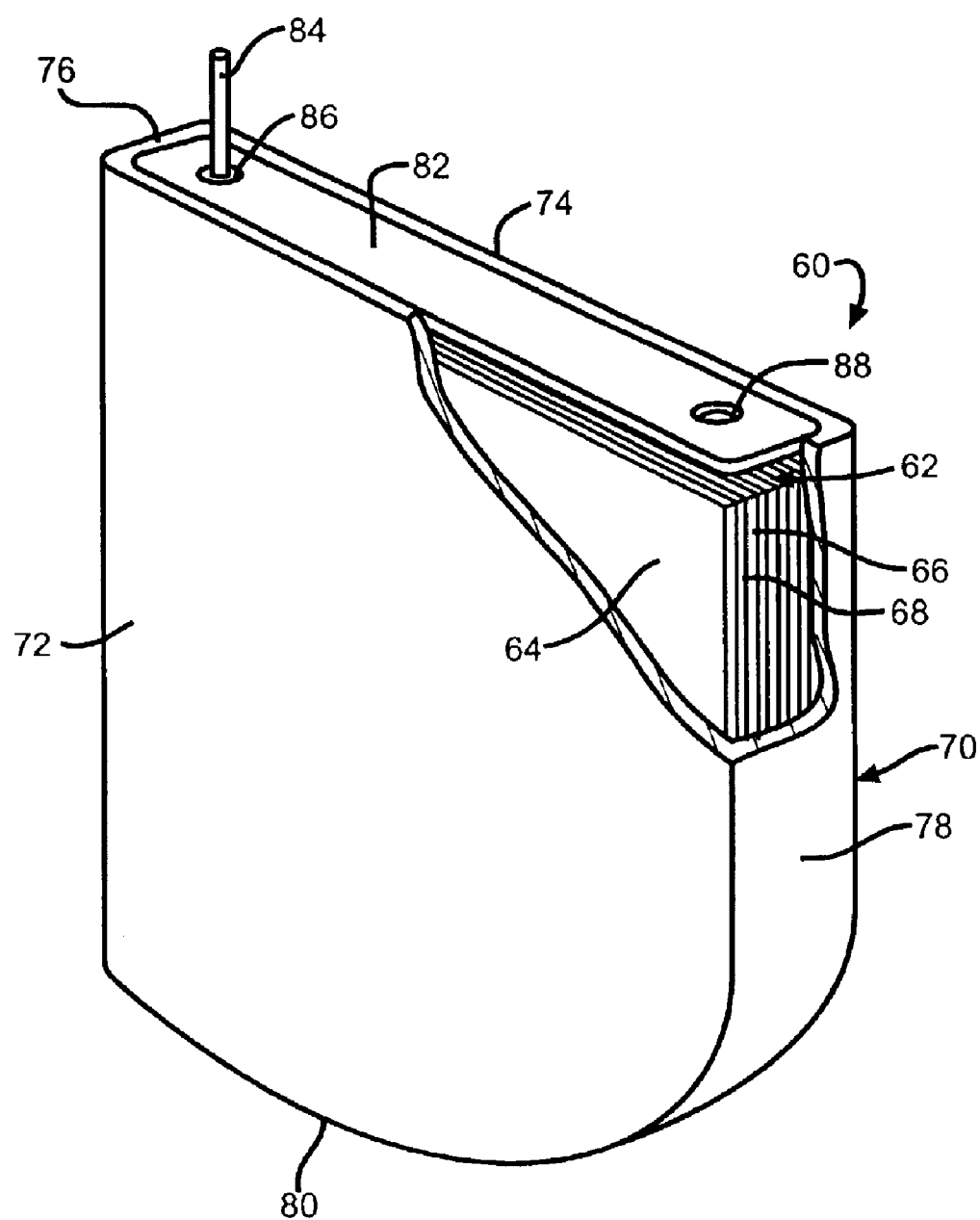
FIG. 3 is a perspective view, partly broken away, of an irregularly shaped casing housing a multiplate electrode assembly according to the present invention.

FIG. 3 is a perspective view, partly broken away, of an electrochemical cell 60 comprising a multiplate electrode assembly 62 housed in an irregularly shaped casing according to the present invention. The electrode assembly 62 comprises a plurality of anode plates 64 in electrical association with a plurality of cathode plates 66 having a separator 68 disposed intermediate each anode and cathode plate to prevent direct physical contact between them. If the cell is intended to be of a case-negative configuration, then the outwardly most plates are of the anode electrode, preferably in direct contact with the inside of a casing 70. The casing may comprise materials such as stainless steel, mild steel, nickel-plated mild steel, titanium, tantalum or aluminum, but not limited thereto, so long as the metallic material is compatible for use with components of the cell.

Figure 1:
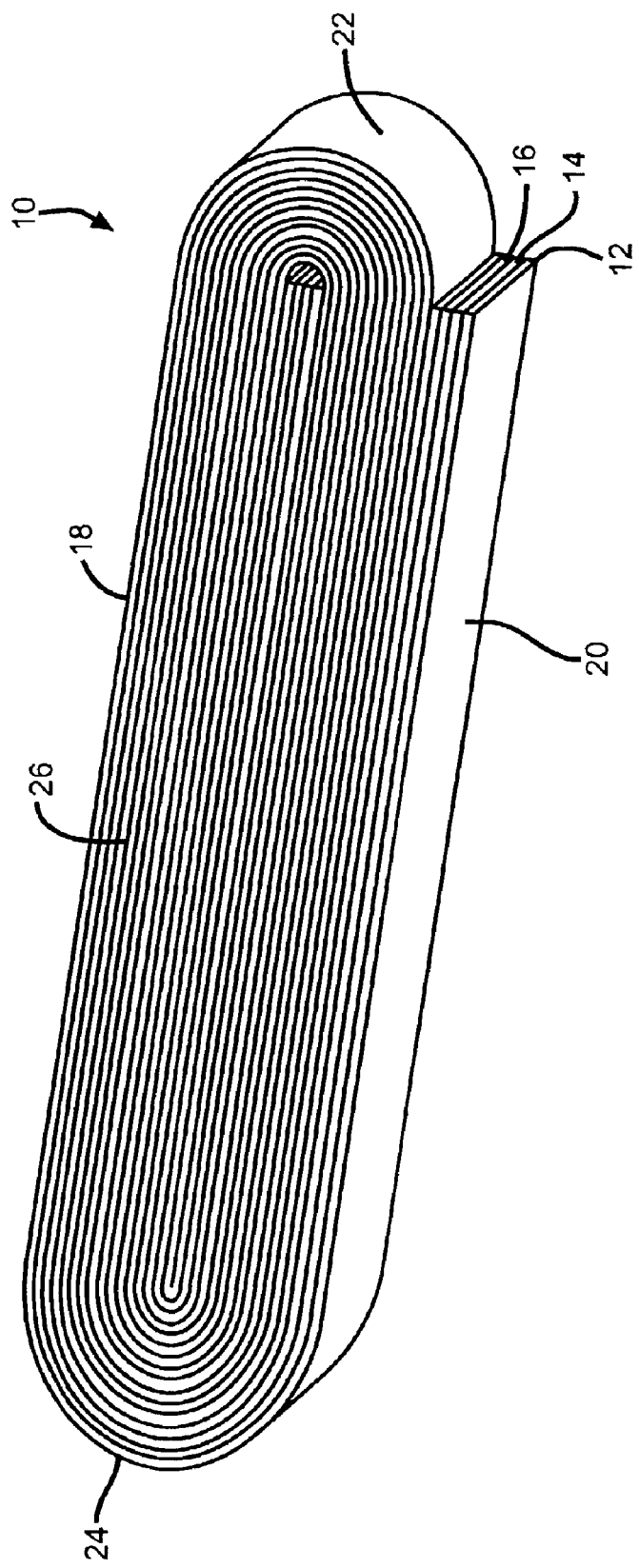
FIG. 1 is a perspective view of a prior art wound electrode assembly.
Figure 2A:
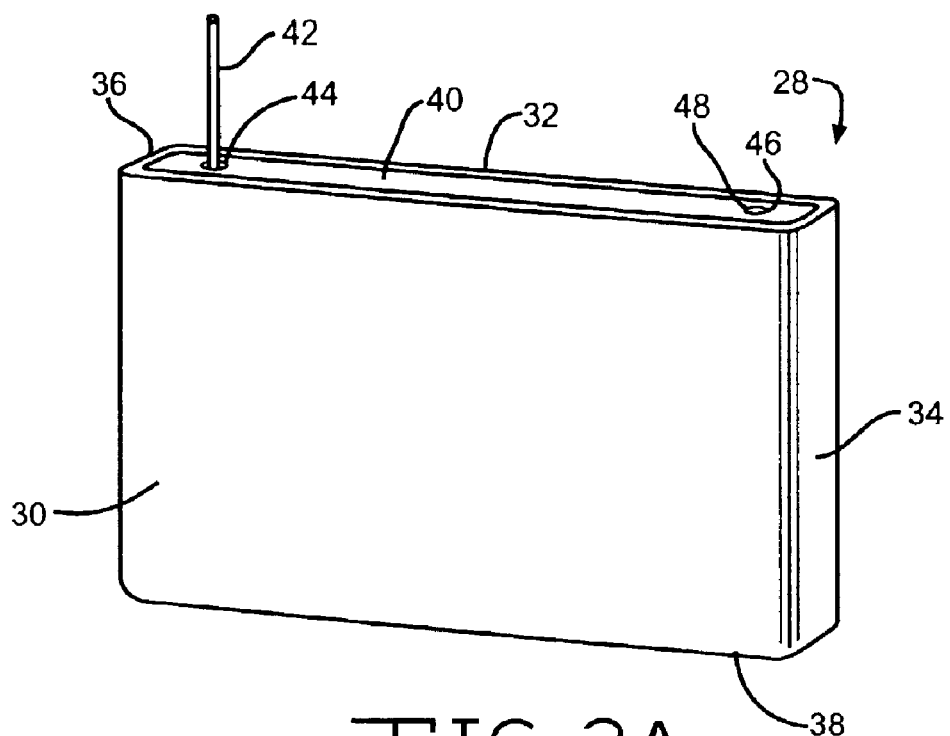
FIG. 2A is a perspective view of a prior art prismatic shaped electrochemical cell.
Figure 2B:
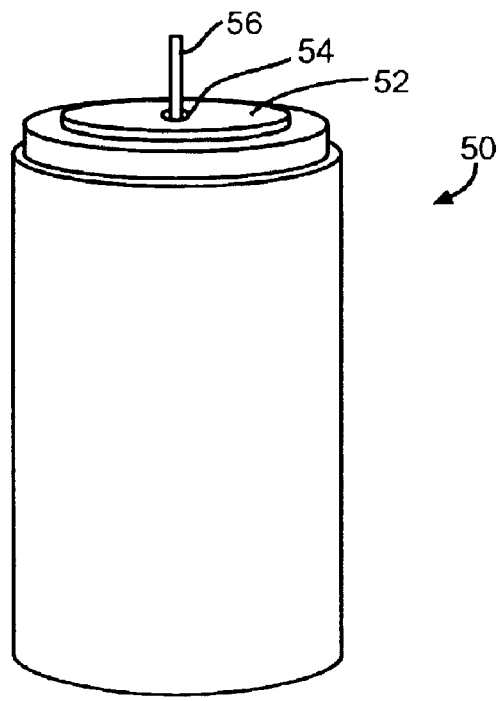
FIG. 2B is a perspective view of a prior art cylindrically shaped electrochemical cell.

The casing 70 is of a deep drawn type having opposed front and back side walls 72 and 74 extending to a left planar end wall 76 and a right planar end wall 78. The left end wall 76 is of a longer length than the right end wall 78. The side walls 72, 74 and end walls 76, 78 each extend to and meet with a bottom wall 80 to form the casing comprising a unitary deep drawn can. Since the left end wall 76 is of a greater length than the right end wall 78, the bottom wall 80 is of an irregular curved shape of a varied radii. This means that if a wound electrode assembly of the type shown in FIG. 1 were housed inside casing 70, there would be a considerable amount of internal volume left unoccupied by active components, especially adjacent to the bottom wall 80. This detracts from volumetric efficiency.

A lid 82 secured to the upper edges of face walls 72, 74 and end walls 76, 78, such as by welding, closes the casing 70. The lid 82 supports a terminal lead 84 insulated from the lid and casing by a glass-to-metal seal 86. There is also an electrolyte fill opening 88 in the lid closed by a closure means, such as a stainless steel ball, as is well known by those skilled in the art. The lead 84 is connected to one of the electrodes, typically the cathode, while the casing 70 and lid 82 serve as the lead for the other electrode, typically the anode. This describes a case-negative cell design. If a case-positive design is desired, lead 84 is connected to the anode plates 64 while the cathode plates 66 are electrically connected to the casing and the lid.

Figure 4:
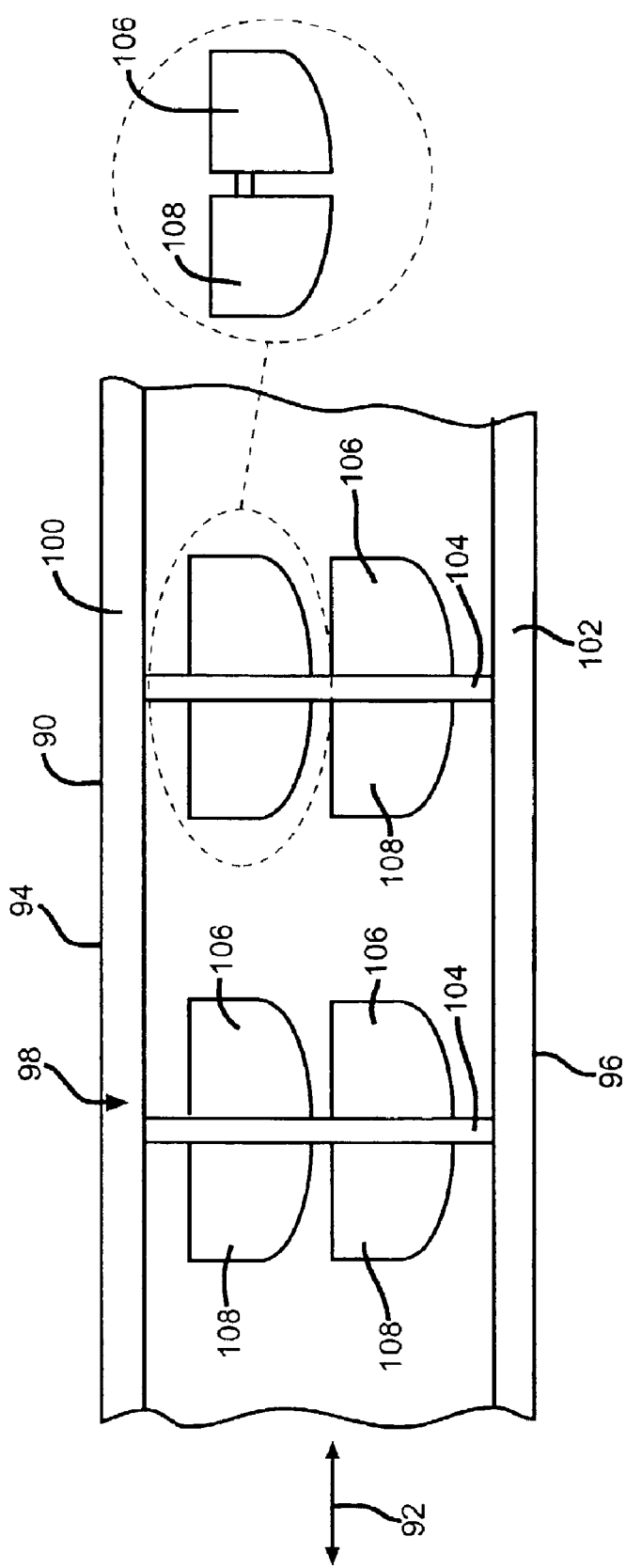
FIGS. 4 and 5 illustrate two processes for building multiplate electrodes according to the present invention.

FIG. 4 illustrates one embodiment for building electrode plates for incorporation into a multiplate electrode assembly according to the present invention. The building process begins with a web 90 of conductive material that is unrolled from a spool (not shown). The web 90 moves along a direction of travel, indicated by arrow 92, and serves as the current collector for one of the electrodes. Whether it is the anode or the cathode electrode is not necessarily important. In that regard, suitable materials for the web 90 include stainless steel, titanium, tantalum, platinum, gold, aluminum, cobalt nickel alloys, highly alloyed ferritic stainless steel containing molybdenum and chromium, and nickel-, chromium-, and molybdenum-containing alloys.

The web 90 is comprised of spaced apart edges 94 and 96 bordering upper and lower major surfaces (only the upper surface 98 is shown in the drawing). Each side of the unwinding web 90 is contacted with an electrode active material mixture (not shown) in selected areas. The electrode active mixture typically comprises an anode or cathode active material, a binder such as a fluoro-resin powder and a conductive diluent such as a powdered carbonaceous material. This mixture in slurry form is sprayed, brushed, rolled, spread or otherwise contacted to the web to coat areas from which electrodes will later be cut.

The coating process leaves selected areas of the web uncoated. These include an upper and a lower border 100 and 102 extending inwardly from the respective upper and lower edges 94 and 96. The borders 100, 102 generally extend the entire usable length of the web 90 and are where tracking wheels contact the web to ensure that it runs in a straight path. The web 90 is also provided with secondary uncoated stripes 104 oriented perpendicularly to the length of the web. The uncoated stripes 104 extend from one border 100 to the other 102 and are spaced at regular intervals along the web 90. The stripes 104 coincide with a connector portion of an electrode current collector connecting between two electrode plates which will be cut from the web, as will be described in detail next. While only one side of the web 90 is shown, it is within the scope of the present invention that the opposite side is coated in an identical, coinciding manner.

The thusly-coated web is then moved through an oven (not shown) to drive off any volatile compounds in the slurry and to cure the electrode active mixture contacted to the substrate. Next, the electrode plates are cut from the web in the precise shape dictated by the casing. This cutting is accomplished by any one of a number of means including laser cutting, stamping, and the like. Preferably, two spaced apart plates 106 and 108, one on either side of a connector portion 110 coinciding with the uncoated stripe 104 are cut out as a unit. The conductive connector 110 spans between the plates 106, 108.

It should be pointed out that the drawing in FIG. 4 is exaggerated to illustrate the present invention. In practice, there is as little selvage as possible left between immediately adjacent electrode plate pairs.

Figure 5:
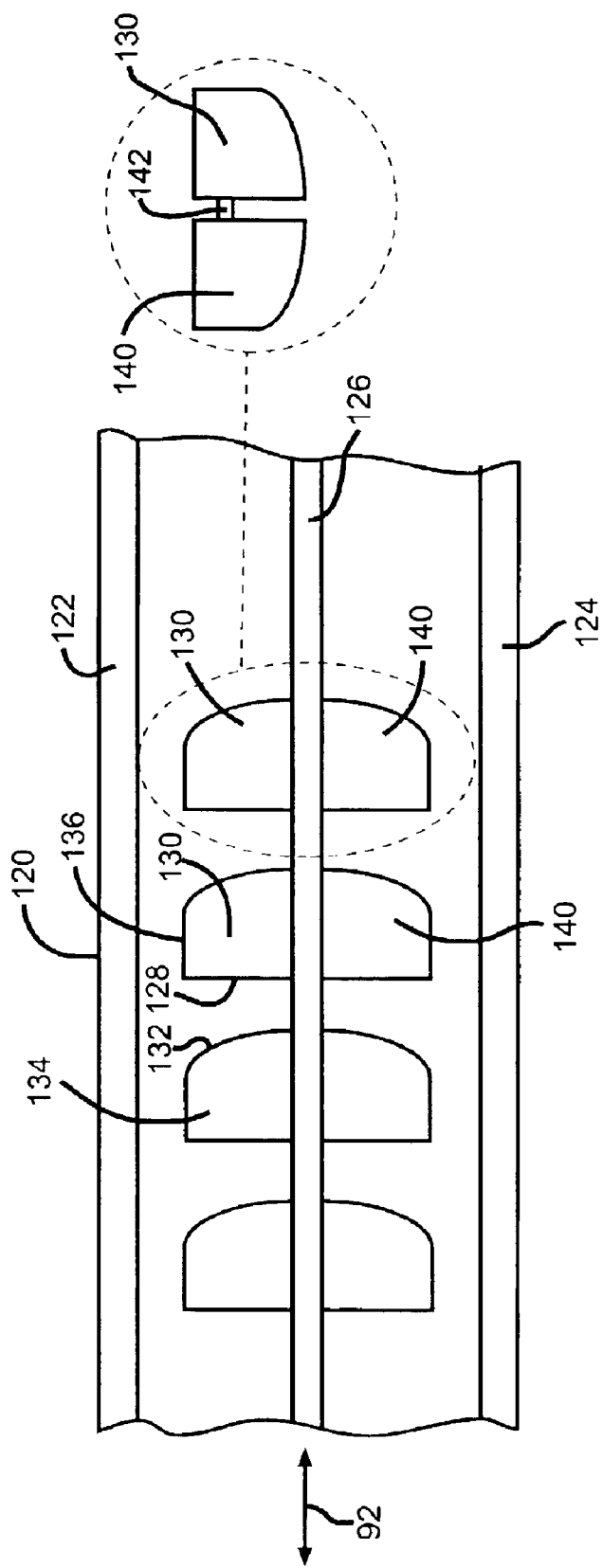

FIG. 5 illustrates an alternate embodiment of a manufacturing process for providing electrode plates according to the present invention. Again, a conductive web 120 is selectively contacted with an electrode active mixture, leaving uncoated upper and lower borders 122 and 124 and an intermediate stripe 126. However, the stripe 126 is aligned along the axis of the web 120, parallel to borders 122, 124, instead of being disposed perpendicular to the longitudinal axis of the web, as in the embodiment of FIG. 4. As before, the opposed sides of the web 120 are coated with an electrode active mixture for either a cathode electrode or an anode electrode, as the production run dictates.

After curing, the electrode plates are cut from the web 120. However, this time the plates are aligned so that the upper edge 128 of one plate 130 is immediately adjacent to the lower edge 132 of another 134 with the opposed ends 136 and 138 of a pair of plates 130, 140 adjacent to the borders 122, 124. Again, the drawing has been exaggerated to illustrate the invention. A connecting portion 142 completes the plate pair 130, 140 where the stripe 126 once resided. In practice, as little selvage as possible is produced by the process.

It is within the scope of the present invention that instead of the just described processes where the electrode active materials are selectively coated in specific locations as the electrode build requirements dictate, a resist coating can be used where active material is not desired. In this case, the stripes 100, 102 and 104 of FIG. 4 and the stripes 122, 124 and 126 of FIG. 5 are first provided with a resist coating. Then, the electrode active material is coated to the web, cured and, finally, the resist is removed leaving the selectively coated webs from which the electrode plates are subsequently cut.

Figure 6:
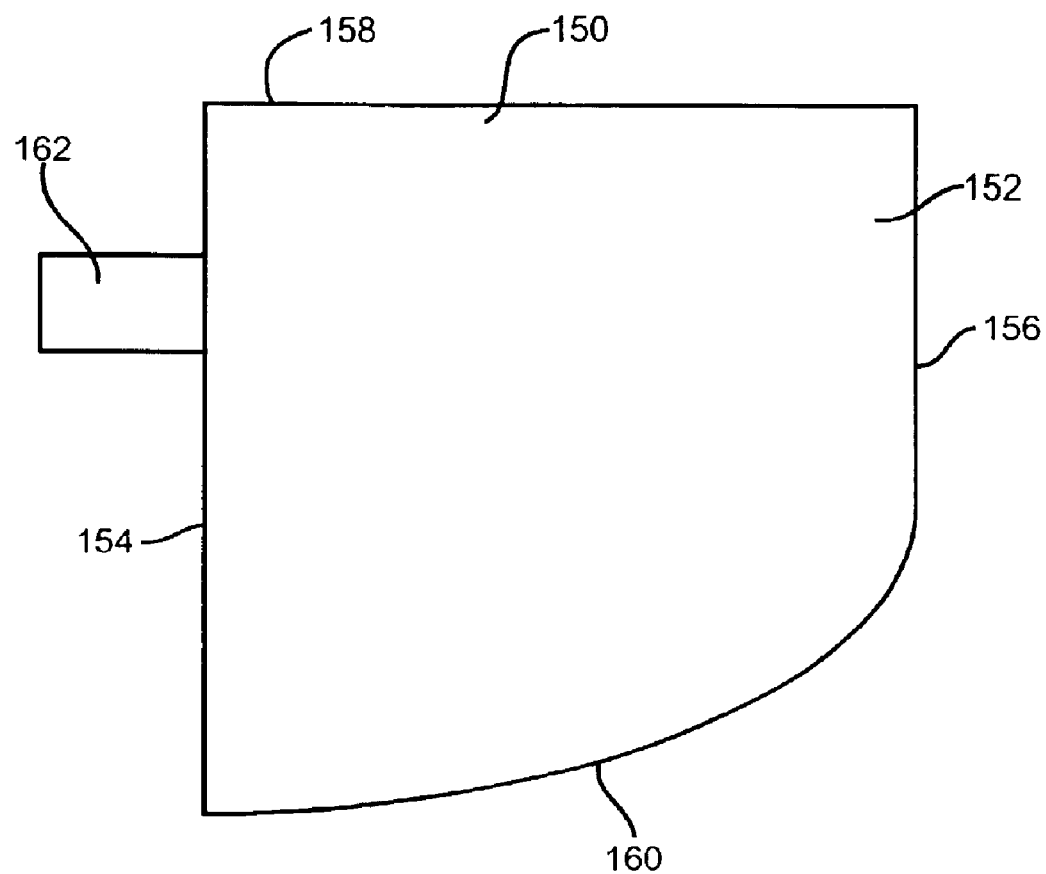
FIG. 6 is an elevational view of an electrode plate produced by the current processes.

FIG. 6 shows an electrode plate 150 that has been produced by either one of the processes shown in FIGS. 4 and 5 and having a shape that is uniquely suited to fit into the casing 70 shown in FIG. 3. The electrode plate 150 comprises opposed major faces (only face 152 shown) extending to a planar left end 154 and a planar right end 156. The right end wall 156 is shorter than the left end 154. The faces 152 and ends 154. 156 extend to an upper side 158 and a bottom side 160. Since the right end 156 is of a shorter length than the left end 154, the bottom side 160 is of an irregular curved shape substantially matched to that of the bottom wall 80 of casing 70. The left and right ends 154, 156 also substantially match the respective walls 76, 78 of the casing 70. There is a similarly shaped companion electrode plate (not shown) hidden behind plate 150 and connected thereto by a conductive connector 162.

Figure 7:
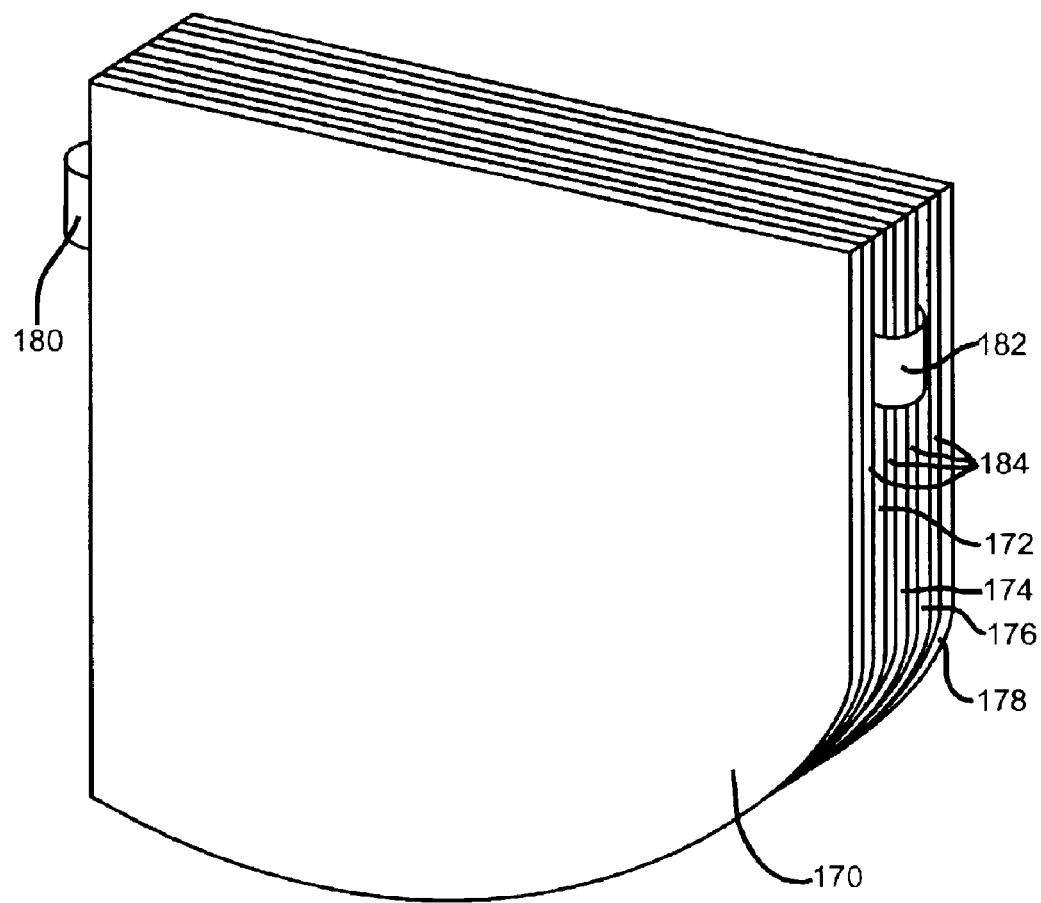
FIG. 7 is a perspective view of a multiplate electrode stack according to the present invention.

The electrode assembly shown in FIG. 7 is then constructed by interleaving an electrode plate of one polarity into the space provided between electrode plates of an opposite polarity that have been folded towards each other. This provides a subassembly of plates as: anode 170/cathode 172/anode 174/cathode 176/anode 178 when two plate pairs of opposite polarity plus an extra anode plate are associated with each other. The number of electrode plates or plate pairs in an assembly can include any number of this subassembly in repeating order. In that respect, connector 180 is of one polarity while connector 182 is of an opposite polarity. A separate material 184 is disposed between adjacent electrode plates to prevent direct physical contact between them, as is well known to those of skill in the art.

After the multiplate electrode assembly is inserted into the casing to substantially occupy the internal volume thereof, a conductive structure connects the connectors 180, 182 to their respective terminals. This may take the form of connecting the anode connector to an anode lead (not shown) welded to the interior of the casing 70 or to the lid 82 for a cell in a case-negative design with the cathode connector welded to the terminal pin 84 insulated from the lid 82 and casing 70 by the glass-to-metal seal 86. Additionally, the anode lead may be pinched between the lid and the casing and subsequently fused as they are hermetically welded together. Methods of welding include, but are not limited to, resistance welding, plasma welding, ultrasonic welding and laser welding. Regardless of where the anode lead is welded to the casing 70, the lid 82 is hermetically sealed thereto.

While the present invention in FIGS. 4 and 5 is shown as being useful for manufacturing electrode plates as pairs with an intermediate connector member, it should not be so limited. The present invention can also be used to produce electrode structures of three or more plates connected together by intermediate connector members. In that case, an exemplary method for forming the electrode assembly is described in U.S. Pat. Nos. 5,776,628 to Kraft et al. and 6,120,563 to Kraft et al. These patents are assigned to the assignee of the present invention and incorporated herein by reference. Also, only one plate and associated connector are cut from the web, if desired.

Figure 8:
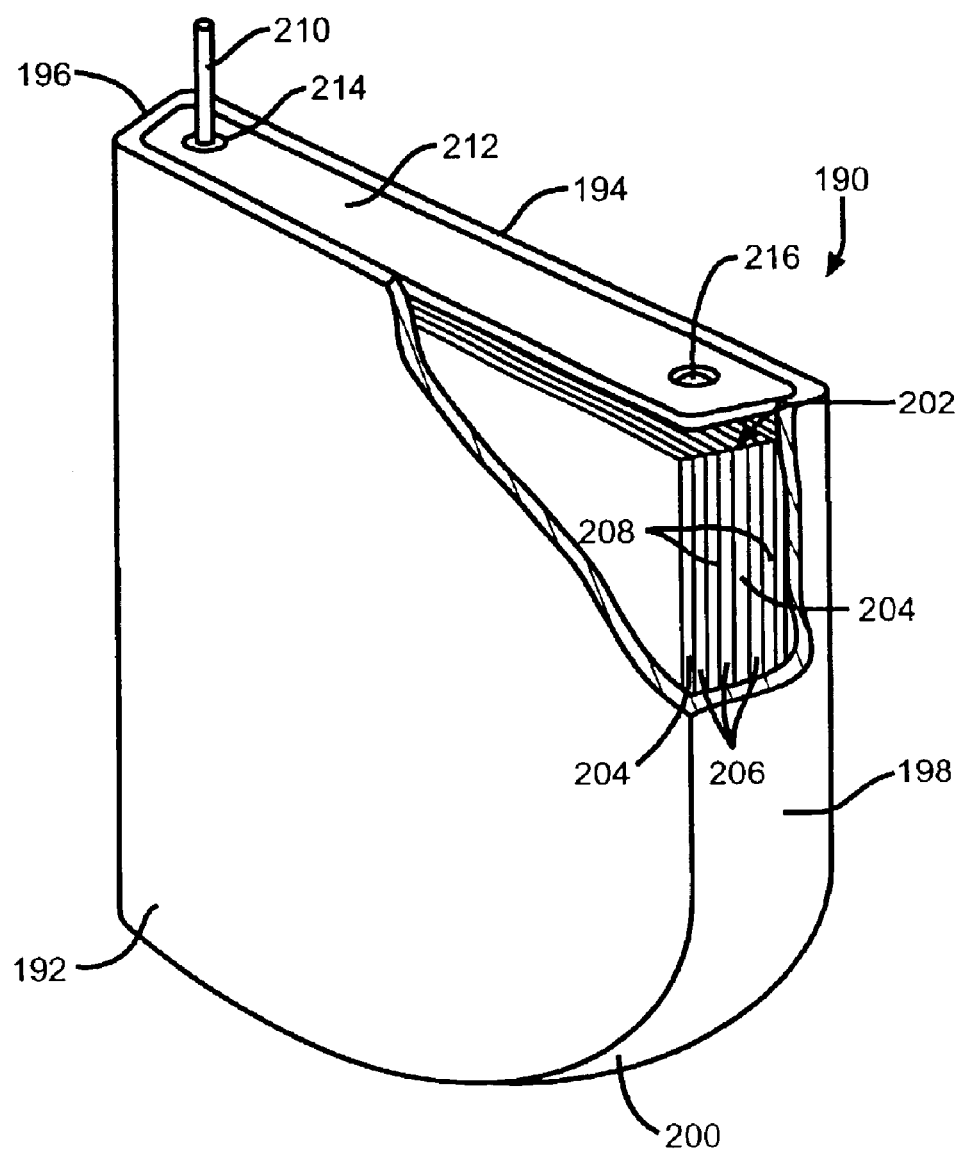
FIG. 8 is a perspective view, partly broken away, of an alternate embodiment of an irregularly shaped casing housing a multiplate electrode assembly according to the present invention.

FIG. 8 shows an alternate embodiment of a electrochemical cell comprising a casing 190 according to the present invention. Casing 190 has opposed front and back side walls 192 and 194 extending to a left end wall 196 and a right end wall 198. The end walls 196 and 198 are planar, although that is not necessary. Left end wall 196 is longer in length than right end wall 198, and both extend to a bottom wall 200 of an irregularly curved shape. In FIG. 3, the opposed front and back side walls 72 and 74 are of substantially the same shape and size. In contrast, the front and back side walls 192 and 194 are of a similar shape, but the front wall is smaller in area than the back side wall 194. This means that the side walls 196 and 198 and the bottom wall angle toward each other.

The electrode assembly 202 housed inside the casing 190 is comprised of alternating cathode plates 204 and anode plates 206 sandwiching a separator 208. Because of the angled side walls 192, 194 and bottom wall 200, the anode and cathode plates adjacent to the back side wall 194 having a larger surface area than those adjacent to the front side wall 192. A case-positive electrode assembly is shown with the cathode plates 204 electrically connected to the casing 190 while the anode plates 206 are connected to a terminal pin 210 supported in a lid 212 hermetically sealed to the casing. The terminal pin is insulated from the lid and casing by a glass-to-metal seal 214. A closure means 216 seals the electrolyte fill opening.

In a further embodiment of the invention, the front and back side walls 192 and 194 are of a dissimilar shape. In still another embodiment, the side walls 192 and 194 are both of a dissimilar size and shape.

The electrode assembly is useful in an electrochemical cell of either a primary chemistry or a secondary, rechargeable chemistry. For both the primary and secondary types, the cell comprises an anode active metal selected from Groups IA, IIA and IIIB of the Periodic Table of the Elements, including lithium, sodium, potassium, etc., and their alloys and intermetallic compounds including, for example, Li—Si, Li—Al, Li—B, Li—Mg and Li—Si—B alloys and intermetallic compounds. The preferred metal comprises lithium. An alternate negative electrode comprises a lithium alloy, such as lithium-aluminum alloy. The greater the amount of aluminum present by weight in the alloy, however, the lower the energy density of the cell.

For a primary cell, the anode is a thin metal sheet or foil of the lithium material, pressed or rolled on a metallic anode current collector, i.e., preferably comprising nickel, to form the negative electrode. In the exemplary cell of the present invention, the negative electrode has an extended tab or lead of the same material as the current collector, i.e., preferably nickel, integrally formed therewith such as by welding and contacted by a weld to a cell case of conductive material in a case-negative electrical configuration. Alternatively, the negative electrode may be formed in some other geometry, such as a bobbin shape, cylinder or pellet to allow an alternate low surface cell design.

In secondary electrochemical systems, the anode or negative electrode comprises an anode material capable of intercalating and de-intercalating the anode active material, such as the preferred alkali metal lithium. A carbonaceous negative electrode comprising any of the various forms of carbon (e.g., coke, graphite, acetylene black, carbon black, glassy carbon, etc.) which are capable of reversibly retaining the lithium species, is preferred for the anode material. A "hairy carbon" material is particularly preferred due to its relatively high lithium-retention capacity. "Hairy carbon" is a material described in U.S. Pat. No. 5,443,928 to Takeuchi et al., which is assigned to the assignee of the present invention and incorporated herein by reference. Graphite is another preferred material. Regardless of the form of the carbon, fibers of the carbonaceous material are particularly advantageous because they have excellent mechanical properties that permit them to be fabricated into rigid electrodes that are capable of withstanding degradation during repeated charge/discharge cycling. Moreover, the high surface area of carbon fibers allows for rapid charge/discharge rates.

A typical negative electrode for a secondary cell is fabricated by mixing about 90 to 97 weight percent "hairy carbon" or graphite with about 3 to 10 weight percent of a binder material, which is preferably a fluoro-resin powder such as polytetrafluoroethylene (PTFE), polyvinylidene fluoride (PVDF), polyethylenetetrafluoroethylene (ETFE), polyamides, polyimides, and mixtures thereof. This negative electrode admixture is provided on a current collector such as of a nickel, stainless steel, or copper foil or screen by casting, pressing, rolling or otherwise contacting the admixture thereto.

In either the primary cell or the secondary cell, the reaction at the positive electrode involves conversion of ions that migrate from the negative electrode to the positive electrode into atomic or molecular forms. For a primary cell, the cathode active material comprises a carbonaceous chemistry or at least a first transition metal chalcogenide constituent which may be a metal, a metal oxide, or a mixed metal oxide comprising at least a first and a second metals or their oxides and possibly a third metal or metal oxide, or a mixture of a first and a second metals or their metal oxides incorporated in the matrix of a host metal oxide. The cathode active material may also comprise a metal sulfide.

Carbonaceous active materials are preferably prepared from carbon and fluorine, which includes graphitic and nongraphitic forms of carbon, such as coke, charcoal or activated carbon. Fluorinated carbon is represented by the formula $(CF_x)_n$ wherein x varies between about 0.1 to 1.9 and preferably between about 0.5 and 1.2, and $(C_2F)_n$ wherein n refers to the number of monomer units which can vary widely.

The metal oxide or the mixed metal oxide is produced by the chemical addition, reaction, or otherwise intimate contact of various metal oxides, metal sulfides and/or metal elements, preferably during thermal treatment, sol-gel formation, chemical vapor deposition or hydrothermal synthesis in mixed states. The active materials thereby produced contain metals, oxides and sulfides of Groups IB, IIB, IIIB, IVB, VB, VIB, VIIB and VIII, which include the noble metals and/or other oxide and sulfide compounds. A preferred cathode active material is a reaction product of at least silver and vanadium.

One preferred mixed metal oxide is a transition metal oxide having the general formula $SM_xV_2O_y$ where SM is a metal selected from Groups IB to VIIB and VIII of the Periodic Table of Elements, wherein x is about 0.30 to 2.0 and y is about 4.5 to 6.0 in the general formula. By way of illustration, and in no way intended to be limiting, one exemplary cathode active material comprises silver vanadium oxide having the general formula $Ag_xV_2O_y$ in any one of its many phases, i.e., β-phase silver vanadium oxide having in the general formula x=0.35 and y=5.8, γ-phase silver vanadium oxide having in the general formula x=0.80 and y=5.40 and ε-phase silver vanadium oxide having in the general formula x=1.0 and y=5.5, and combination and mixtures of phases thereof. For a more detailed description of such cathode active materials, reference is made to U.S. Pat. No. 4,310,609 to Liang et al., which is assigned to the assignee of the present invention and incorporated herein by reference.

Another preferred composite transition metal oxide cathode material includes $V_2O_z$ wherein $z \leq 5$ combined with $Ag_2O$ having silver in either the silver(II), silver(I) or silver(0) oxidation state and CuO with copper in either the copper(II), copper(I) or copper(0) oxidation state to provide the mixed metal oxide having the general formula $Cu_xAg_yV_2O_z$, (CSVO). Thus, the composite cathode active material may be described as a metal oxide-metal oxide-metal oxide, a metal-metal oxide-metal oxide, or a metal-metal-metal oxide and the range of material compositions found for $Cu_xAg_yV_2O_z$ is preferably about $0.01 \leq z \leq 6.5$. Typical forms of CSVO are $Cu_{0.16}Ag_{0.67}V_2O_z$ with z being about 5.5 and $Cu_{0.5}Ag_{0.5}V_2O_z$ with z being about 5.75. The oxygen content is designated by z since the exact stoichiometric proportion of oxygen in CSVO can vary depending on whether the cathode material is prepared in an oxidizing atmosphere such as air or oxygen, or in an inert atmosphere such as argon, nitrogen and helium. For a more detailed description of this cathode active material, reference is made to U.S. Pat. Nos. 5,472,810 to Takeuchi et al. and 5,516,340 to Takeuchi et al., both of which are assigned to the assignee of the present invention and incorporated herein by reference.

In addition to the previously described fluorinated carbon, silver vanadium oxide and copper silver vanadium oxide, $Ag_2O$, $Ag_2O_2$, $CuF_2$, $Ag_2CrO_4$, $MnO_2$, $V_2O_5$, $MnO_2$, $TiS_2$, $Cu_2S$, FeS, $FeS_2$, copper oxide, copper vanadium oxide, and mixtures thereof are contemplated as useful active materials.

In secondary cells, the positive electrode preferably comprises a lithiated material that is stable in air and readily handled. Examples of such air-stable lithiated cathode active materials include oxides, sulfides, selenides, and tellurides of such metals as vanadium, titanium, chromium, copper, molybdenum, niobium, iron, nickel, cobalt and manganese. The more preferred oxides include $LiNiO_2$, $LiMn_2O_4$, $LiCoO_2$, $LiCu_{0.92}Sn_{0.08}O_2$ and $LiCo_{1-x}Ni_xO_2$. A preferred secondary couple is of a carbonaceous anode material and a lithium cobalt oxide cathode active material.

To charge such secondary cells, the lithium ion comprising the positive electrode is intercalated into the carbonaceous negative electrode by applying an externally generated electrical potential to the cell. The applied recharging electrical potential serves to draw lithium ions from the cathode active material, through the electrolyte and into the carbonaceous material of the negative electrode to saturate the carbon. The resulting $Li_xC_6$ negative electrode can have an x ranging between 0.1 and 1.0. The cell is then provided with an electrical potential and is discharged in a normal manner.

An alternate secondary cell construction comprises intercalating the carbonaceous material with the active lithium material before the negative electrode is incorporated into the cell. In this case, the positive electrode body can be solid and comprise, but not be limited to, such active materials as manganese dioxide, silver vanadium oxide, titanium disulfide, copper oxide, copper sulfide, iron sulfide, iron disulfide and fluorinated carbon. However, this approach is compromised by problems associated with handling lithiated carbon outside of the cell. Lithiated carbon tends to react when contacted by air or water.

The above described cathode active materials, whether of a primary or a secondary chemistry, are incorporation into an electrochemical cell by mixing one or more of them with a binder material. Suitable binders are powdered fluoropolymers; more preferably powdered polytetrafluoroethylene or powdered polyvinylidene fluoride present at about 1 to about 5 weight percent of the cathode mixture. Further, up to about 10 weight percent of a conductive diluent is preferably added to the cathode mixture to improve conductivity. Suitable materials for this purpose include acetylene black, carbon black and/or graphite or a metallic powder such as powdered nickel, aluminum, titanium and stainless steel. The preferred cathode active mixture thus includes a powdered fluoro-polymer binder present at about 1 to 5 weight percent, a conductive diluent present at about 1 to 5 weight percent and about 90 to 98 weight percent of the cathode active material. Cathode components are prepared by contacting the cathode active mixture in the form of a slurry onto one of the previously described conductive webs 90, 120 serving as a current collector. The preferred cathode current collector material is titanium, and most preferably the titanium cathode current collector has a thin layer of graphite/carbon paint applied thereto.

In order to prevent internal short circuit conditions, the cathode is separated from the Group IA, IIA or IIIB anode by a suitable separator material. The separator is of electrically insulative material, and the separator material also is chemically unreactive with the anode and cathode active materials and both chemically unreactive with and insoluble in the electrolyte. In addition, the separator material has a degree of porosity sufficient to allow flow there through of the electrolyte during the electrochemical reaction of the cell. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric microporous film, non-woven glass, polypropylene, polyethylene, glass fiber materials, ceramics, a polytetrafluoroethylene membrane commercially available under the designation ZITEX (Chemplast Inc.), a polypropylene membrane commercially available under the designation CELGARD (Celanese Plastic Company, Inc.) and a membrane commercially available under the designation DEXIGLAS (C. H. Dexter, Div., Dexter Corp.).

The electrochemical cell of the present invention further includes a nonaqueous, ionically conductive electrolyte that serves as a medium for migration of ions between the anode and the cathode electrodes during the electrochemical reactions of the cell. The electrochemical reaction at the electrodes involves conversion of ions in atomic or molecular forms that migrate from the anode to the cathode. Thus, nonaqueous electrolytes suitable for the present invention are substantially inert to the anode and cathode materials, and they exhibit those physical properties necessary for ionic transport, namely, low viscosity, low surface tension and wettability.

A suitable electrolyte has an inorganic, ionically conductive salt dissolved in a nonaqueous solvent, and more preferably, the electrolyte includes an ionizable alkali metal salt dissolved in a mixture of aprotic organic solvents comprising a low viscosity solvent and a high permittivity solvent. The inorganic, ionically conductive salt serves as the vehicle for migration of the anode ions to intercalate or react with the cathode active materials. Preferably, the ion forming alkali metal salt is similar to the alkali metal comprising the anode. In the case of an anode comprising lithium, the electrolyte salt is a lithium-based salt selected from $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, $LiSCN$, $LiO_3SCF_3$, $LiC_6F_5SO_3$, $LiO_2CCF_3$, $LiSO_6F$, $LiB(C_6H_5)_4$, $LiCF_3SO_3$, and mixtures thereof.

Low viscosity solvents useful with the present invention include esters, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy, 2-methoxyethane (EME), ethyl methyl carbonate (EMC), methyl propyl carbonate, ethyl propyl carbonate, diethyl carbonate (DEC), dipropyl carbonate, and mixtures thereof, and high permittivity solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL), N-methyl-pyrrolidinone (NMP), and mixtures thereof. In the present invention, the preferred anode for a primary cell is lithium metal and the preferred electrolyte is 0.8M to 1.5M $LiAsF_6$ or $LiPF_6$ dissolved in a 50:50 mixture, by volume, of propylene carbonate as the preferred high permittivity solvent and 1,2-dimethoxyethane as the preferred low viscosity solvent.

A preferred electrolyte for a secondary cell of an exemplary carbon/$LiCoO_2$ couple comprises a solvent mixture of EC:DMC:EMC:DEC. Most preferred volume percent ranges for the various carbonate solvents include EC in the range of about 20% to about 50%; DMC in the range of about 12% to about 75%; EMC in the range of about 5% to about 45%; and DEC in the range of about 3% to about 45%. In a preferred form of the present invention, the electrolyte activating the cell is at equilibrium with respect to the mole ratio of DMC:EMC:DEC. This is important to maintain consistent and reliable cycling characteristics. It is known that due to the presence of low-potential (anode) materials in a charged cell, an un-equilibrated molar mixture of DMC::DEC in the presence of lithiated graphite ($LiC_6$~0.01 V vs $Li/Li^+$) results in a substantial amount of EMC being formed. When the concentrations of DMC, DEC and EMC change, the cycling characteristics and temperature rating of the cell change. Such unpredictability is unacceptable. This phenomenon is described in detail in U.S. patent application Ser. No. 10/232,166, filed Aug. 30, 2002, which is assigned to the assignee of the present invention and incorporated herein by reference. Electrolytes containing the quaternary carbonate mixture of the present invention exhibit freezing points below −50° C., and lithium ion secondary cells activated with such mixtures have very good cycling behavior at room temperature as well as very good discharge and charge/discharge cycling behavior at temperatures below −40° C.

FIG. 7 shows the respective anode and cathode plates having substantially similar shapes and sizes. However, this is for the purpose of simplicity. In practice, it is beneficial in a secondary cell to have the peripheral extent of the carbonaceous anode extending beyond that of the cathode. That way, there is always a portion of the anode opposite the lithiated cathode active material so that as the cell is being recharged, the lithium ions intercalate into the carbonaceous anode material and do not plate out as dendritic formations. Dendrites are undesirable as they can lead to cell shorting. If the case-positive design shown in FIG. 8 is of a secondary chemistry, the cathode plate immediately adjacent to the front side wall 192 is of a lesser area than the anode plate which it faces to thereby prevent dendrites from forming.

The glass used in the glass-to-metal seals is of a corrosion resistant type having up to about 50% by weight silicon such as CABAL 12, TA 23, FUSITE 425 or FUSITE 435. The positive terminal leads preferably comprise titanium although molybdenum, aluminum, nickel alloy, or stainless steel can also be used. The cell lids are typically of a material similar to that of the casing.

It is appreciated that various modifications to the present inventive concepts described herein may be apparent to those of ordinary skill in the art without departing from the spirit and scope of the present invention as defined by the herein appended claims.

What is claimed is:

1. An electrochemical cell, which comprises:
   a) an anode comprising an anode current collector comprising a right end wall and a left end wall, both extending from an upper wall to a bottom wall and being intermediate first and second major sides with an anode material contacted to at least one of the major sides to provide at least one anode plate;
   b) a cathode comprising a cathode current collector comprising a right end wall and a left end wall, both extending from an upper wall to a bottom wall and being intermediate first and second major sides with a cathode active material contacted to at least one of the major sides to provide at least one cathode plate;
   c) a casing comprising spaced apart first and second major casing side walls extending to and meeting with an end wall, the casing end wall and first and second major casing side walls extending to an opening, wherein the casing end wall comprises a right end wall portion and a left end wall portion, both extending from the opening to a bottom wall portion with one of the right and left end wall portions being longer than the other such that the bottom wall curves upwardly from the longer one of the right and left end wall portions to the other end wall portion and wherein the at least one major anode plate and the at least one major cathode plate are of substantially the same area as the respective first and second casing major side walls with their respective current collectors each having their bottom walls curving upwardly from the aligned longer ones of the right and left end walls to the other end walls, wherein the coinciding longer ones of the right and left end walls of the respective anode and cathode current collectors are aligned with the longer one of the right and left end wall portions of the casing;
   d) a separator disposed intermediate the anode material of the at least one anode plate facing the cathode active material of the at least one cathode plate;
   e) a lid closing the opening of the casing;
   f) first and second terminals connected to the respective anode and cathode; and
   g) an electrolyte in the casing to activate the anode and cathode.

2. The electrochemical cell of claim 1 wherein there are at least two anode plates and at least one cathode plate.

3. The electrochemical cell of claim 2 wherein the anode plates are connected to each other by an anode connector and the cathode plate resides intermediate the two anode plates.

4. The electrochemical cell of claim 1 wherein the first and second major casing side walls are of substantially the same area.

5. The electrochemical cell of claim 1 wherein the first and second major casing side walls are of substantially the same shape.

6. The electrochemical cell of claim 1 wherein the first and second major casing side walls are of substantially the same shape, but of dissimilar areas such that at least the right and left end walls angle toward each other.

7. The electrochemical cell of claim 6 wherein there are at least two anode plates and at least one cathode plate intermediate the anode plates with a first one of the anode plates positioned adjacent to the first major casing side wall and a second one of the anode plates positioned adjacent to the second major casing side wall and wherein the first and second anode plates are themselves of dissimilar area sizes, but of a similar area as the respective first and second casing side walls to which they are closest.

8. The electrochemical cell of claim 7 wherein the first and second anode plates are of substantially the same shape and of a similar area as the respective dissimilarly sized first and second major casing side walls.

9. The electrochemical cell of claim 6 wherein there are at least two cathode plates and at least one anode plate intermediate the cathode plates with a first one of the cathode plates positioned adjacent to the first major casing side wall and a second one of the cathode plates positioned adjacent to the second major casing side wall and wherein the first and second cathode plates are themselves of dissimilar area sizes, but of a similar area as the respective first and second major casing side walls to which they are closest.

10. The electrochemical cell of claim 9 wherein the first and second cathode plates are of substantially the same shape and of a similar area as the respective dissimilarly sized first and second major casing side walls.

11. The electrochemical cell of claim 1 wherein the casing houses at least two anode plates having at least one cathode plate interleaved therebetween and wherein the at least two anode plates are of substantially the same shape and area as the respective first and second casing major side walls with the at least one cathode plate being of substantially the same shape, but of a lesser size than both anode plates.

12. The electrochemical cell of claim 1 wherein the lid comprises an electrolyte fill opening and supports a pin as one of the terminals.

13. The electrochemical cell of claim 1 wherein the cell is either of a primary lithium/silver vanadium oxide chemistry or a secondary chemistry comprising a carbonaceous anode material and lithium cobalt oxide cathode active material.

14. An electrochemical cell, which comprises:
   a) an anode comprising an anode current collector with an anode material contacted thereto to provide at least two anode plates;
   b) a cathode comprising a cathode current collector with a cathode active material contacted thereto to provide at least one cathode plate;
   c) a casing comprising spaced apart first and second major casing side walls extending to and meeting with an end wall, the casing end wall and first and second major casing side walls extending to an opening, wherein the casing end wall comprises a right end wall portion and a left end wall portion, both extending from the opening to a bottom wall portion with one of the right and left end wall portions being longer than the other such that the bottom wall curves upwardly from the longer one of the right and left end wall portions to the other end, wherein the first and second major casing side walls are of substantially the same shape, but of dissimilar area sizes such that at least the right and left end walls angle toward each other, and wherein the at least two anode plates are of substantially the same shape and area as the respective first and second casing major side walls with the at least one cathode plate being intermediate them and of substantially the same shape as both anode plates;

d) a separator disposed intermediate the anode plates and the at least one cathode plate;

e) a lid closing the opening of the casing;

f) first and second terminals connected to the respective anode and cathode; and g) an electrolyte in the casing to activate the anode and cathode.

15. The electrochemical cell of claim 14 wherein the at least one cathode plate is of substantially the same shape, but of a lesser size than both anode plates.

16. A method for providing an electrochemical cell, comprising the steps of:

a) providing an anode comprising an anode current collector comprising a right end wall and a left end wall, both extending from an upper wall to a bottom wall and being intermediate first and second major sides and then contacting an anode material to at least one of the major sides of the anode current collector to provide at least one anode plate;

b) providing a cathode comprising a cathode current collector comprising a right end wall and a left end wall, both extending from an upper wall to a bottom wall and being intermediate first and second major sides and then contacting a cathode active material to at least one of the major sides of the cathode current collector to provide at least one cathode plate;

c) providing a casing comprising spaced apart first and second major casing side walls extending to and meeting with an end wall, with the casing end wall and first and second major casing side walls extending to an opening, wherein the casing end wall comprises a right end wall portion and a left end wall portion, both extending from the opening to a bottom wall portion with one of the right and left end wall portions being longer than the other such that the bottom wall curves upwardly from the longer one of the right and left end wall portions to the other end wall portion and wherein the at least one major anode plate and the at least one major cathode plate are of substantially the same area as the respective first and second casing major side walls with their respective current collectors each having their bottom walls curving upwardly from the aligned longer ones of the right and left end walls to the other end walls, wherein the coinciding longer ones of the right and left end walls of the respective anode and cathode current collectors are aligned with the longer one of the right and left end wall portions of the casing;

d) providing a cell stack comprising a separator disposed intermediate the anode material of the at least one anode plate facing the cathode active material of the at least one cathode plate;

e) housing the cell stack inside the casing;

f) closing the opening of the casing with a lid secured thereto;

g) connecting respective terminals to each of the anode and the cathode; and h) filling an electrolyte into the casing to activate the anode and the cathode.

17. The method of claim 16 including providing at least two anode plates and at learnt one cathode plate.

18. The method of claim 17 including connecting the anode plates to each other by an anode connector with the cathode plate residing intermediate the two anode plates.

19. The method of claim 16 including providing the first and second major casing side walls being of substantially the same area.

20. The method of claim 16 including providing the first and second major casing side walls being of substantially the same area.

21. The method of claim 16 including providing the first and second major casing side walls being of substantially the same shape, but of dissimilar areas such that at least the right and left end walls angle toward each other.

22. The method of claim 21 including providing at least two anode plates and at leas one cathode plate intermediate the anode plates and positioning a first one of the anode plates adjacent to the first major casing side wall and a second one of the anode plates adjacent to the second major casing side wall, the first and second major anode plates being of dissimilar area sizes, but of a similar area as the respective first and second casing side walls to which they are closest.

23. The method of claim 22 including providing the first and second anode plates having substantially the same shape and area as the respective dissimilarly sized first and second major casing side walls.

24. The method of claim 21 including providing at least two cathode plates and at least one anode plate intermediate the cathode plates with a first one of the cathode plates positioned adjacent to the first major casing side wall and a second one of the cathode plates positioned adjacent to the second major casing side wall, the first and second cathode plates being of dissimilar area sizes, but of a similar area as the respective first and second major casing side walls to which they are closest.

25. The method of claim 24 including providing the first and second cathode plates having substantially the same shape and being of a similar area as the dissimilarly sized respective first and second major casing side walls.

26. The method of claim 16 including providing the casing bottom wall portion being of a changing radius.

27. The method of claim 16 including providing the casing housing at least two anode plates having at least one cathode plate interleaved therebetween, wherein the at least two anode plates are of substantially the same shape and area as the respective first and second casing major side walls with the at least one cathode plate being of substantially the same shape, but of a lesser size than both anode plates.

* * * * *